United States Patent [19]

Abraham

[11] Patent Number: 5,200,339
[45] Date of Patent: Apr. 6, 1993

[54] PROTEASES CAUSING ABNORMAL DEGRADATION OF AMYLOID β-PROTEIN PRECURSOR

[76] Inventor: Carmela R. Abraham, 5 Blodgett Rd., Lexington, Mass. 02173

[21] Appl. No.: 681,093

[22] Filed: Apr. 5, 1991

Related U.S. Application Data

[63] Continuation-in-part of Ser. No. 568,806, Aug. 17, 1990, abandoned.

[51] Int. Cl.$^5$ .......................... C12N 9/48; C12Q 1/37; A61K 37/547
[52] U.S. Cl. .................................. 435/212; 435/814; 435/23; 424/94.64
[58] Field of Search .......................... 435/212, 23, 814; 424/94.64

[56] References Cited

PUBLICATIONS

Nelson et al., (1990) J. Biol. Chem., 265(7), 3836–3843.
Nelson et al. (1989) Soc. Neurosci. Abst., 15, 330, Abst. #135.9.
Abraham et al. (1991) Biochem. Biophys. Res. Comm., 174(2), 790–796.
Siman et al. (1990) J. Neurosci., 10(7), 2400–2410.
Barrett (1981) Meth. Enzymol., 80, 561–564, Acad. Press, N.Y.
Cataldo et al. (1990) Proc. Nat. Acad. Sci. USA, 87, 3861–3865.
Matsumoto et al. (1991) Biochem. Biophys. Res. Comm., 175(2), 361–365.
Justice et al. (1987) J. Cell. Biochem., 34, 227–238.
Abraham et al. (1989) Cell, 52, 487–501.
Bowen, et al., "Cathepsin A in Human Brain and Spleen", 1973, Biochem. J., vol. 131, pp. 417–419.

Primary Examiner—David M. Naff
Assistant Examiner—Jon P. Weber
Attorney, Agent, or Firm—Choate, Hall & Stewart

[57] ABSTRACT

A proteolytic factor is capable of cleaving β-protein precursor at a site near the β-protein N-terminus. Also, a method for treating Alzheimer's disease in a patient includes steps of reducing β-protein precursor proteolysis outside the β-protein domain at a site near the β-protein N-terminus. Also, a method for purifying an enzyme from a sample includes steps of incubating the sample with a labelled substrate of the enzyme or with a labelled fragment of a substrate to which the enzyme binds, treating the sample with a crosslinking agent to crosslink any enzyme-substrate complexes in the sample, and recovering labelled complexes. Also, a method for diagnosis in a subject of a disease characterized by accumulation of amyloid includes determining the level, in a sample of tissue or body fluid from the subject, of an AD proteolytic factor. Also, a method for screening for an agent useful in treatment of a disease characterized by accumulation of amyloid includes steps of incubating an AD protease with a peptide having an amino acid sequence corresponding to the sequence spanning the β-protein N-terminus in the presence of a candidate agent, and determining the degradation of the peptide.

2 Claims, 7 Drawing Sheets

Cathepsin G   H  S  E ▲ V  K ▲ M ▲ D ▲ A  E  F
                    3      100  46   7

CASP          H  S  E  V  K ▲ M ▲ D ▲ A  E  F
                 ▲            21   18   34
                 9

PROTEASES CAUSING ABNORMAL DEGRADATION OF AMYLOID β-PROTEIN PRECURSOR

BACKGROUND OF THE INVENTION

This invention was made during the course of work supported in part by the U.S. Government, and the Government has certain rights in the invention.

This application is a continuation-in-part of my co-pending application U.S. Ser. No. 568,806, filed Aug. 17, 1990 now abandoned.

This invention relates to treatment of Alzheimer's disease.

The brains of persons having Alzheimer's disease and Down's syndrome and, to a far lesser extent, the brains of normal aged persons exhibit abnormal extracellular proteinaceous deposits, termed amyloid. Amyloid deposits are thought to be trophic or toxic to their surroundings.

Amyloid deposits are found in the center of senile plaques and in the blood vessels in the brains of Alzheimer's disease ("AD") patients. The major component of brain amyloid is the β-protein, a 4 Kd (39–42 amino acids) fragment (see, e.g., G. G. Glenner et al. (1984), *Biochem. Biophys. Res. Comm.*, Vol. 12, pp. 1131–35; C. L. Masters et al. (1985), *Proc. Natl. Acad. Sci. USA*, Vol. 82, pp. 4245–49; D. J. Selkoe et al. (1986), *Jour. Neurochem.*, Vol. 46, pp. 1820–34; A. Roher et al. (1986), *Proc. Natl. Acad. Sci. USA*, Vol. 83, pp. 2662–66, all hereby incorporated herein by reference), derived from a larger, 110–135 Kd β-protein precursor ("β-PP") (see, e.g., D. Goldgaber et al. (1987), *Science*, Vol. 235, pp. 877–80; J. Kang et al. (1987), *Nature*, Vol. 325, pp. 733–36; N. K. Robakis et al. (19897), *Proc. Natl. Acad. Sci. USA*, Vol. 84, pp. 4190–94; R. E. Tanzi et al. (1987), *Science*, Vol. 235, pp. 880–83, all hereby incorporated herein by reference). In addition to and tightly associated with the β-protein, brain amyloid also contains a serine protease inhibitor, α1-antichymotrypsin ("ACT").

Certain β-PP transcripts include a domain homologous to the Kunitz-type protease inhibitors (described, for example, in N. Kitaguchi et al. (1988), *Nature*, Vol. 331, pp. 530–32; P. Ponte et al. (1988), *Nature*, Vol. 311, pp. 525–27; R. E. Tanzi et al. (1988), *Nature*, Vol. 331, pp. 528–30). The normal physiologic C-terminal cleavage that releases the secreted form of β-PP (PN2) occurs within the β-protein domain, and outside the putative membrane domain.

M. Tsudo et al. (1987), *Proc. Natl. Acad. Sci. USA*, Vol. 84, pp. 4215–18) describe crosslinking a ligand and a receptor site for the ligand by treatment with disuccinimidyl suberate ("DSS").

SUMMARY OF THE INVENTION

We have discovered proteolytic factors from the brain of AD patients, here termed "AD proteolytic factors". According to the invention accumulation of the β-protein is a consequence of an alternative degradation pathway that results in abnormal β-PP processing, and one or more of the AD proteolytic factors participates in this abnormal pathway.

In general, in one aspect, the invention features an AD proteolytic factor capable of cleaving β-protein precursor at a site near the β-protein N-terminus. In preferred embodiments the AD proteolytic factor is capable of cleaving β-PP at a site outside the β-protein domain and near the β-protein N-terminus, more preferably at a site following lysine or at a site following methionine; a first AD proteolytic factor includes a calcium-activated protease, preferably a serine protease; activity of the serine AD proteolytic factor is inhibited by PN2 and by ACT; a second AD proteolytic factor includes a cysteine protease; the cysteine protease is a metalloprotease, $Ca^{2+}$- or $Mg^{2+}$-dependent (and possibly $Zn^{2+}$-dependent) having a molecular weight about 43–68 kDa.

In another general aspect, the invention features a method for treating Alzheimer's disease in a patient, by reducing β-protein precursor proteolysis at a site near the β-protein N-terminus. In preferred embodiments, the method includes administering to the patient an inhibitor that inhibits proteolysis at a site outside the β-protein domain of β-PP and at or near the β-protein N-terminus, and preferably inhibits proteolysis in the vicinity of the β-protein N-terminus, preferably by inhibiting the proteolytic activity of a proteolytic factor that acts at such a site; the inhibitor is capable of passing the blood-brain barrier, and the inhibitor can be administered, for example, parenterally (intravascularly or intramuscularly) or orally.

In another general aspect, the invention features a method for diagnosis in a subject of a disease characterized by accumulation of amyloid, and particularly of Alzheimer's Disease, by determining the level, in a sample from the subject, such as a tissue or fluid sample, of an AD proteolytic factor.

In another general aspect, the invention features a method for screening for an agent useful in treatment of a disease characterized by accumulation of amyloid, by incubating an AD protease with a peptide having an amino acid sequence corresponding to the sequence spanning the β-protein N-terminus in the presence of the candidate agent, and determining degradation of the peptide. A candidate agent may be useful in treating such a disease where peptide degradation by the AD protease is less in the presence of the candidate agent than would have been expected under the same or similar reaction conditions in the absence of the candidate agent.

In preferred embodiments the peptide has an amino acid sequence that includes a 10-amino acid sequence spanning the β-protein N-terminus, and more preferably beginning five or six amino acids upstream from the N-terminus.

In another general aspect, the invention features a method for purifying an enzyme from a sample, and particularly a proteolytic enzyme, by incubating the sample with a substrate of the enzyme or with a fragment of the substrate to which the enzyme binds, treating the sample with DSS to crosslink any enzyme-substrate complexes in the sample, and recovering the complexes. In preferred embodiments the substrate or substrate fragment is labelled (more preferably radiolabelled).

DESCRIPTION OF PREFERRED EMBODIMENTS

Drawings

Isolation and Purification of Cysteine AD Proteolytic Factor

An AD proteolytic factor according to the invention can be identified in and isolated from a tissue homogenate using, for example, conventional liquid chromatography.

The following is a detailed description, presented by way of example, of a protocol for identifying, isolating, and partially characterizing an AD proteolytic factor from brain homogenate. It will be appreciated that protocols varying in detail from the protocol described here may be used to isolate and purify AD proteolytic factors that are within the scope of the invention.

Generally, the protocol includes steps of homogenizing the tissue; making a crude separation using affinity liquid chromatography; further separating using a first DEAE-ion exchange column, followed by a gel filtration column, followed by a second DEAE-ion exchange column; and dialyzing and finally purifying using affinity liquid chromatography. The description also includes protocols for characterizing the purified AD proteolytic factor (molecular weight; substrate specificity) and for screening for useful inhibitors of the activity.

The protocol described in detail below has been used successfully to isolate and purify a cysteine AD protease from AD brain homogenate. This cysteine AD protease cleaves the P1 peptide after Met. It has a molecular weight about 43-68 kDa, and is a metalloprotein, being $Ca^{2+}$- or $Mg^{2+}$-dependent, and possibly $Zn^{2+}$-dependent. Apparently, most cysteine protease inhibitors effectively inhibit the AD cysteine protease purified from AD brain homogenates according to the following protocol.

Brain Homogenates

Brain tissue from AD patients is homogenized in ice-cold 5×(volume/weight) Tris-Cl buffer containing 1% Triton X-100 and 1 mM dithiothreitol ("DTT") in a Waring blender. After homogenization, the solution is stirred for 30 minutes on ice, and then centrifuged at 100,000×g for 60 minutes. The supernatants representing the soluble enzyme are subjected to ammonium sulfate fractionation: 0-25%, 25-50%, 50-75%, >75%, by slowly adding ammonium sulfate salt to the supernatants while stirring on ice. The solution is then stirred for 20 minutes and centrifuged in a Sorval RC-58 refrigerated centrifuge at 10,000×g for 30 minutes. After the third centrifugation, the three precipitates from the ammonium sulfate fractionation steps are redissolved in Tris-Cl and 1 mM DTT, pH 7.4 buffer, and all fractions are dialyzed extensively against the same buffer before further steps.

Synthetic Peptide Substrate

To assay for a protease or proteases that cleave in the vicinity of the N-terminus of the β-protein, an $^{125}$I-labeled peptide having the sequence HSEVKMDAEF (peptide "P1") was synthesized corresponding to the β-PP sequence flanking that site. The peptide starts five amino acids upstream from the N-terminus (the aspartic acid, "D", is at the N-terminus of the β-protein) and extends across the putative cleavage site into the β-protein itself; histidine, "H", was added for purpose of radioiodination (that is, histidine replaces the isoleucine that appears at that site in the native β-protein). Labeled peptide was incubated with brain fractions of varying purity and the resulting fragments were separated by thin layer chromatography ("TLC"); N-terminal fragments were detected by autoradiography. The site of cleavage for an unknown cleavage product is then determined either by direct sequence analysis of the cleavage product, or by comparing the unknown cleavage product with cleavage products resulting from a known enzyme such as cathepsin G. Proteolytic activities from AD brain can also be examined by Western blots using full length β-PP derived from rat brain as a substrate.

Assay for Synthetic Peptide Substrate Degrading Activity

The different protease fractions are monitored for proteolytic activity against iodinated peptide "P1". Incubations are carried out at 37° C. in 50 mM Tris-Cl, pH 7.4, in the presence of 1 mM $MgCl_2$+1 mM DTT. The proteolytic products are separated by TLC on cellulose microcrystalline plates, using n-butanol:pyridine:acetic acid:water, 15:10:3:12 (v/v), as a solvent, followed by autoradiography.

Purification of Cysteine Protease

Affigel Blue Affinity Chromatography

Affigel Blue is preferred for the first chromatographic step, as it purifies the protease pool from serum albumin and a large number of other protein species. Affigel Blue (Bio-Rad) (1.5 cm×33 cm) is equilibrated to 50 mM Tris-Cl+1 mM DTT, pH 7.4, and eluted with a linear gradient of 0 to 0.5M NaCl. The flow rate is 20 ml/hour, and 3 ml fractions are collected.

First DEAE-Ion Exchange Chromatography

A pool from the Affigel Blue containing the protease activity, as detected using TLC, is loaded on a DEAE-Trisacryl M ion exchange column (1.5 cm×10 cm). The column is equilibrated with 50 mM Tris-Cl+1 mM DTT, pH 7.4, and eluted with a linear gradient of 0 to 0.5M NaCl at a flow rate of 20 ml/hour, and 3 ml fractions are collected.

Gel Filtration Chromatography

A protease activity-positive pool from the first DEAE-Trisacryl M gel filtration step is concentrated to 2.5 ml by ultrafiltration through an Amicon filter (PM-10, 10 kDa cutoff) under nitrogen. The concentrated pool is then loaded on a Sephacryl S-200 gel filtration column (2.5 cm×66 cm), equilibrated, and eluted with 50 mM Tris-Cl+1 mM DTT, Ph 7.4. The flow rate is adjusted to 25 ml/hour, and 2.2 ml fractions are collected.

Second DEAE-Ion Exchange Chromatography

The pool from the Sephacryl S-200 column containing the protease activity is chromatographed on a second DEAE-Trisacryl M ion exchange column (1.5 cm×4.5 cm) with a gradient of 0 to 0.5M NaCl in 50 mM Tris-Cl+1 mM DTT, pH 7.4. The flow rate is adjusted to 20 ml/h, and 2.2 ml fractions are collected.

Thiopropyl Sepharose 6B Affinity Chromatography

In a final step, the pool from the second DEAE-Trisacryl M gel filtration step containing the protease activity is concentrated to 3 ml by ultrafiltration as before. The concentrated pool is dialyzed overnight in two changes of 500 ml 50 mM Tris-Cl, pH 7.4, to remove the DTT. The thiopropyl sepharose 6B resin (0.4 g) is washed with degassed 50 mM Tris-Cl, pH 7.4, followed by 50 mM Tris-Cl+0.3M NaCl, pH 7.4, and 2 ml of the following: 50 mM Tris-Cl+5 mM 2-mercaptoethanol, pH 7.4, and 50 mM Tris-Cl+10 mM 2-mercaptoethanol, pH 7.4. The flow rate is adjusted to 4 ml/hour, and 2.2 ml fractions are collected.

Molecular Weight Determination

The molecular weight of the protease can be estimated by gel filtration using a Sephacryl S-200 (2.5 cm×66 cm) column equilibrated with 50 mM Tris-Cl+1 mM DTT, pH 7.4. The column is eluted with the same buffer at 25 ml/hour, collecting 2.2 ml fractions. The fractions are assayed for proteolytic activity as described above. Protein standards for calibration of the column include β-amylase (200,000 Da), alcohol dehydrogenase (150,000 Da), albumin (66,000 Da), carbonic anhydrase (29,000 Da), and cytochrome C (12,400 Da).

The apparent molecular weight of the protease can also be determined by SDS-PAGE. Molecular weight standards include: Myosin (H-chain) (228,000 Da), phosphorylase B (109,600 Da), bovine serum albumin (70,000 Da), ovalbumin (44,100 Da) and carbonic anhydrase (27,900 Da).

Assay for Inhibition of Peptide P1 Degradation by AD Cysteine Protease

To examine the effects of various protease inhibitor reagents on the synthetic peptide P1-degrading activity, the proteolytically active sample is incubated with the appropriate amount of a putative inhibitor reagent for 60 min. at 4° C., and assayed as described above for remaining proteolytic activity against peptide P1. Control reactions using no inhibitor reagent or containing only the solvent of the reagent are included.

Stock solutions of PMSF are dissolved in 2-propanol, E-64 in dimethylsulfoxide (DMSO), and 1,10 O-phenanthroline and benzamidine-HCl in ethanol. Iodoacetamide, Na-iodoacetate, EGTA, EDTA, bestatin, HMB, and leupeptin are dissolved in double distilled water.

Assay for Substrate Specificity of Purified Cysteine Protease Pool

To examine the substrate specificity of the purified protease pool, aliquots of the purified active fraction were electrophoresed on SDS-substrate gels, containing 1 mg/ml casein or gelatin. The protease pool was mixed on a 1:1 ratio with 2×Laemmli sample buffer without mercaptoethanol and loaded on a 12% SDS polyacrylamide gel containing 2×the usual amount of ammonium persulfate. Electrophoresis was carried out at 4° C. at 20 mA. After electrophoresis, the SDS was removed by shaking the gel in 2.5% Triton X-100 for 30 min. at 25° C. The gel was then incubated in 50 mM Tris-Cl+1 mM CaCl$_2$ for 2 days at 37° C. while shaking. The gel was stained in 0.5% Coomassie Blue and destained.

Radiolabelling Cysteine AD Protease

The proteolytic activity of the purified protease pool made as described above is strongly inhibited by the cysteine protease inhibitor NEM. The protease was labelled with $^{14}$C NEM and the sample was analyzed using SDS-PAGE and autoradiography, as follows. Because $^{14}$C NEM is provided in n-pentane, the NEM solution was added to an equal volume of double distilled water and the n-pentane was evaporated with a gentle stream of nitrogen gas before use. The protease pool solution was incubated with $^{14}$C NEM (6.7 mM final concentration NEM) at 4° C. for 2 hours. After incubation, the solution was mixed with an equal volume of 2×sample buffer and then electrophoresed on a 12% SDS acrylamide gel, generally as described in U.K. Laemmli (1970), *Nature*, Vol. 227, pp. 680–85. Following electrophoresis, the gel was washed in 40% (v/v) methanol, 10% (v/v) acetic acid for 30 min, and then was washed in Enlightning solution (New England Nuclear) for 30 min, and then was dried under vacuum and heat. The gel was then exposed to film for 2 weeks using an intensifying screen. The cysteine AD protease becomes radiolabelled by virtue of its being bound to the labelled NEM inhibitor.

Characterization of Substrate of Cysteine Protease

The activity of purified AD cysteine protease obtained as described above was also assayed against a number of chromogenic substrates and full length β-PP. The protease was incubated with 2 mM substrate solution of MeOSuc-Glu-Val-Lys-Met-pNA, MeOSuc-Ala-Ala-Pro-Met-pNA, Lys-pNA and Met-pNA in 50 mM Tris-Cl, 50 mM CaCl$_2$, 100 mM NaCl, 1 mM DTT, pH 7.9. Changes in absorbance were followed at 410 nm in a Titertek Multiskan ™ ELISA reader. Control reactions contained no enzyme or no substrate. The activity of the protease was tested against full length β-PP purified from rats by incubating them in 50 mM Tris-Cl, pH 7.4, 1.2 mM DTT, 1.7 mM MgCl$_2$. The reactions were incubated overnight at 37° C. and then separated on 7.5% SDS-PAGE gels. The separated polypeptides were transferred to PDVF membranes (Millipore) generally as described in Towbin et al. (1979), *Proc. Natl. Acad. Sci.*, USA, Vol. 76, p. 4350. The blots were immunostained with rabbit anti-β-PP antibody targeted to the area flanking the N-terminus of the β-peptide, and β-PP fragments were detected using goat anti-rabbit alkaline phosphatase and the appropriate color substrate.

Figure 5:
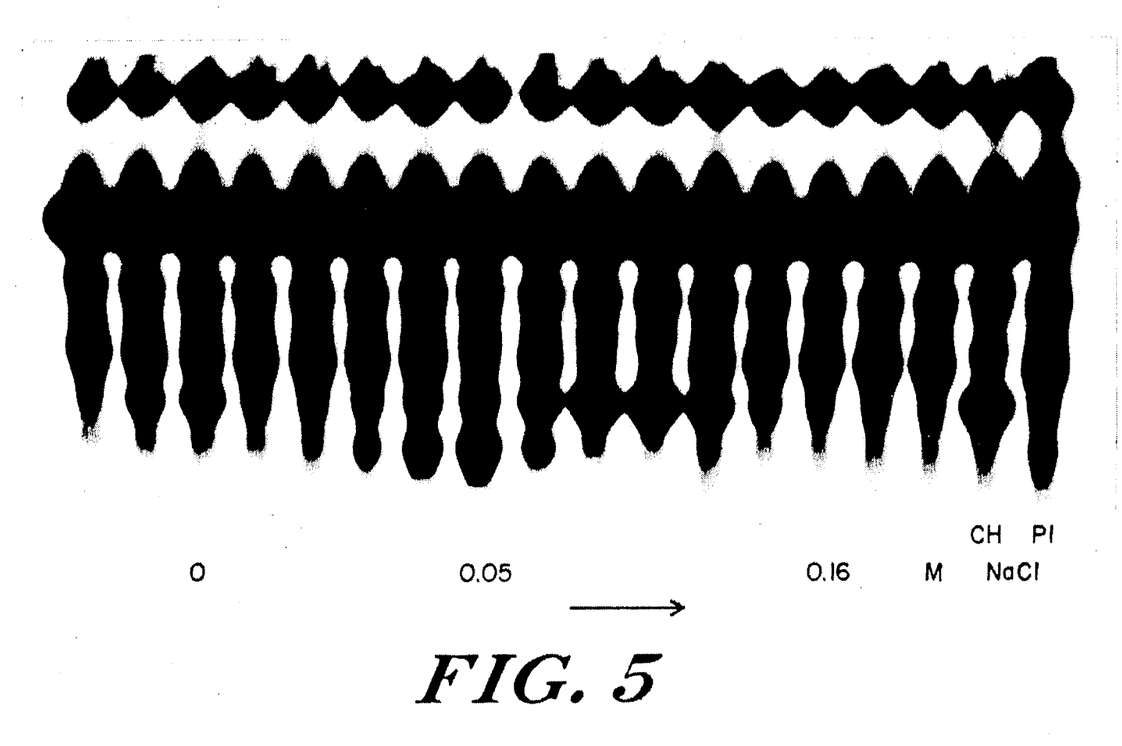
FIG. 5 is a print of a radiograph of a TLC plate showing cysteine protease activity in fractions purified using DEAE-Trisacryl M ion exchange chromatography from brain homogenates from AD patients. Fractions eluted with a linear NaCl gradient, indicated by the arrow at the lower margin of the Figure., were incubated with radioiodinated P1 and separated on TLC. The sequences of uncleaved P1 and of the cleaved products are shown to the right.

FIG. 5 shows cysteine protease activity in fractions purified from brain homogenates from AD patients using DEAE-Trisacryl M ion exchange chromatography as described above.

Figure 6:
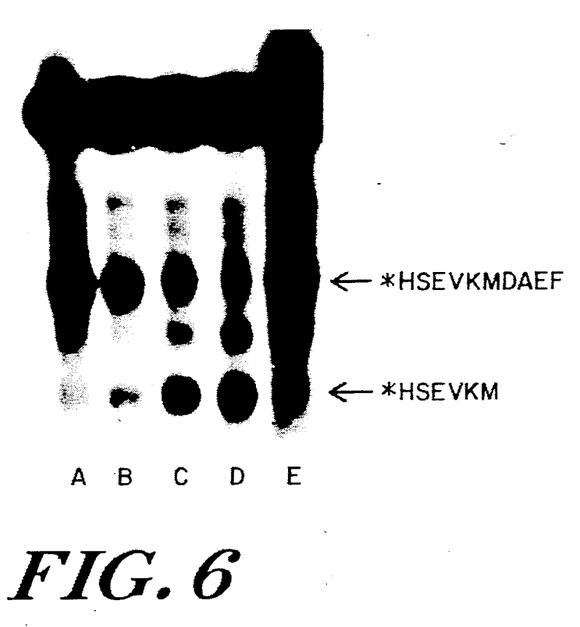
FIG. 6 is a print showing the influence of dithiothreitol ("DTT") on AD cysteine protease activity. Samples having cysteine AD protease activity were incubated with P1 in the presence of increasing concentrations of DTT and the activity was assayed using TLC. Indicated DTT concentrations: A, DTT solvent alone (no DTT); B, 5.0 mM DTT; C, 2.5 mM DTT; D, 1.0 mM DTT; E, peptide alone (no DTT, no solvent).

FIG. 6 shows the effect of DTT on AD cysteine protease activity.

Figure 7:
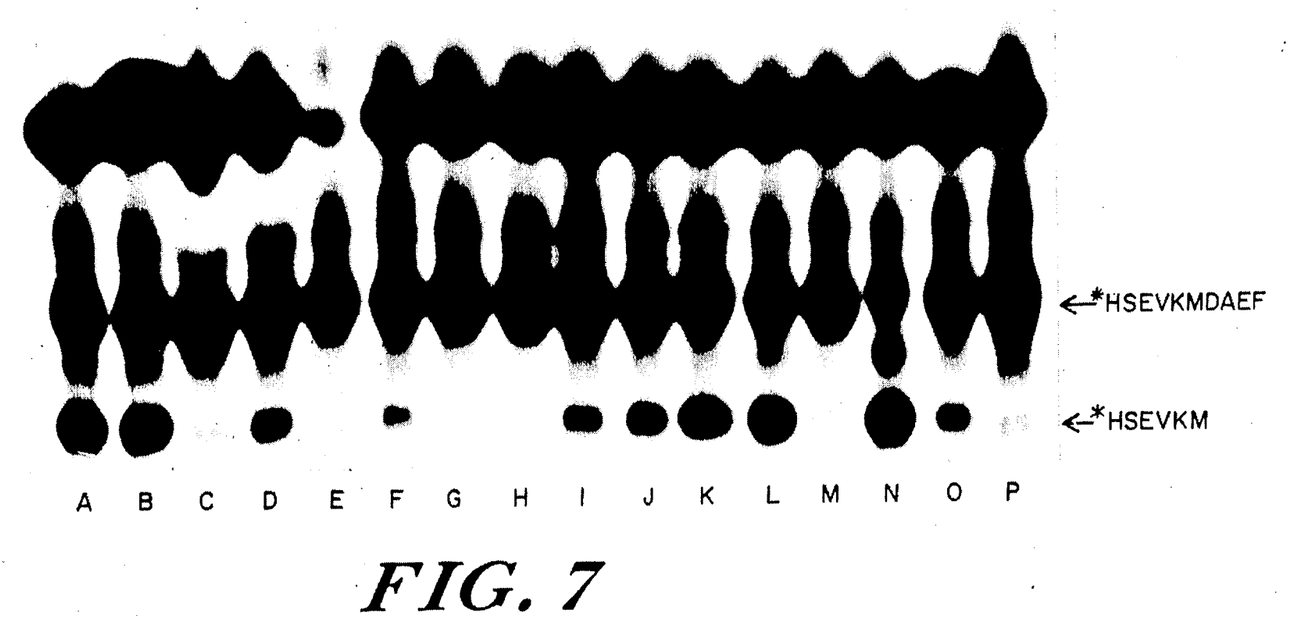
FIG. 7 is a print showing inhibition by various agents on cysteine protease activity in fractions from brain homogenates from AD patients.

FIG. 7 illustrates effects of inhibition by various agents on cysteine protease activity in fractions prepared as described above from brain homogenates from AD patients. The AD cysteine proteolytic factor preparation and the inhibitor (at the indicated concentrations) were incubated at 0° C. for 30 min and then assayed for remaining activity. Lane identifications in FIG. 7 are as follows: lane A, H$_2$O; lane B, Na iodoacetate, 5 mM; lane C, E-64 (Sigma), 0.02 mM; lane D, E-64, 0.01 mM; lane E, p-hydroxymercuribenzoate, 5 mM; lane F, N-ethylmaleimide, 5 mM; lane G, o-phenanthroline, 4 mM; lane H, o-phenanthroline, 1.8 mM; lane I, ethanol; lane J, ethanol/H$_2$O; lane K, PMSF, 5 mM; lane L, bestatin, 0.02 mM; lane M, EGTA, 5 mM; lane N, CaCl$_2$, 2 mM; lane O, DTT, 5 mM; lane P, peptide alone.

Isolation and Characterization of Serine AD Proteolytic Factor

The following is a detailed description of identification and purification of an AD proteolytic factor that includes a Ca$^{2+}$ activated serine protease whose P1 cleaving activity is inhibited by ACT and PN2.

Brain fractions were incubated with the iodinated peptide ($^{125}$I-P1) and treated with disuccinimidyl suberate ("DSS") to crosslink any proteins that were in intimate contact with the peptide, i.e., to crosslink any enzyme-substrate complex (and, in this instance, any protease-substrate complexes. Then, the enzymes were recovered in fractions containing a labelled enzyme-substrate complex, stabilized by the DSS crosslinking, and N-terminal fragments were detected by autoradiography on TLC plates, generally as described above in the detailed protocol for the cysteine AD protease.

Employing these assays (TLC, DSS crosslinking), a specific serine protease activity was partially purified from Alzheimer's brain homogenates by classical liquid chromatography.

Figure 1:
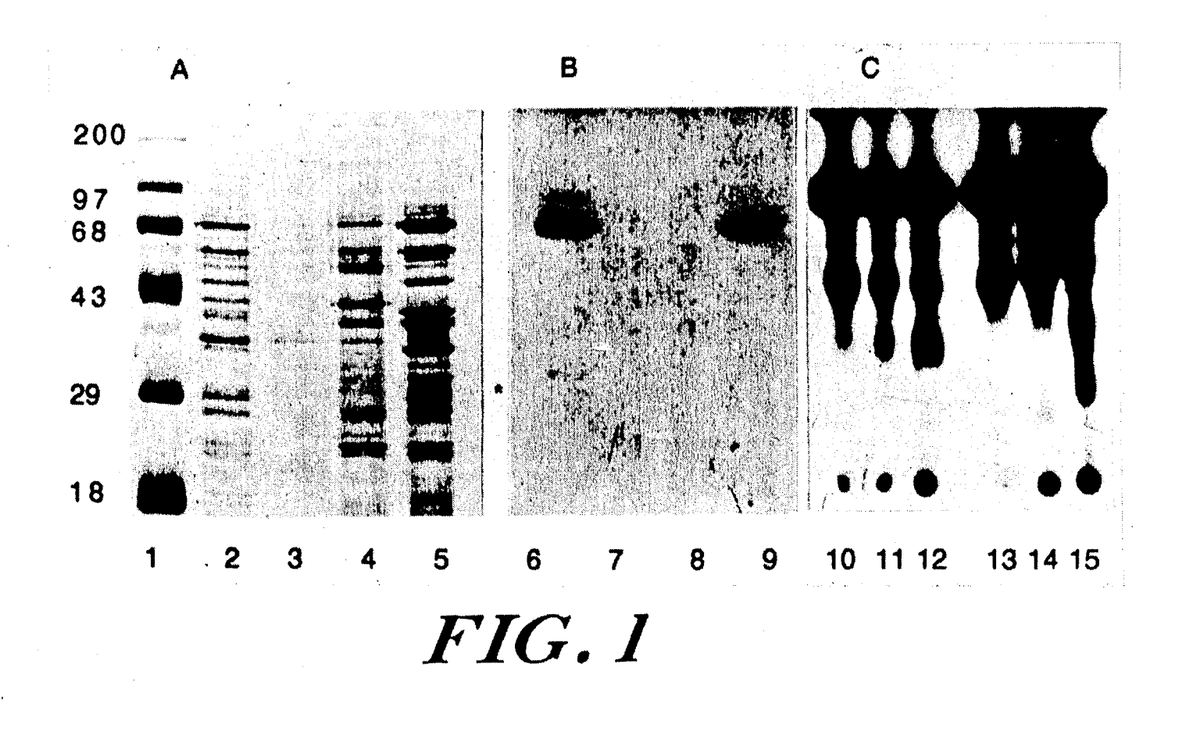
FIG. 1 is a series of prints showing serine protease activity in fractions initially purified from brain homogenates from Alzheimer's disease ("AD") patients. Panel A is a photograph of a coomassie blue stained SDS-PAGE gel showing cleavage products of the iodinated peptide $^{125}$I-HSEVKMDAEF (peptide "P1") following reaction with brain homogenates fractions and cross-linking with disuccinimidyl suberate ("DSS"). Panel B is an X-radiograph of a gel prepared as in Panel A. Panel C is an autoradiograph of a cellulose microcrystalline thin layer chromatography ("TLC") plate showing cleavage products of $^{125}$I-P1 following reaction with brain homogenate fractions.

Results of an initial purification of specific protease activity from Alzheimer's disease brain ("AD brain") are shown in FIG. 1. Brain homogenates were prepared in phosphate buffered saline ("PBS") (20 mM phosphate buffer pH 7.0, 0.15M NaCl) and 1 mM dithiothreitol ("DDT"). and spun at 10,000 g. The supernatant was dialyzed against PBS (20 mM phosphate buffer pH 7.0, 20 mM NaCl) and 1 mM DDT, and applied to DE52-cellulose (Whatman) equilibrated with 10 mM Tris-HCl (pH 7.0, 20 mM NaCl) and 1 mM DDT; the column was extensively washed and bound proteins were eluted with 0.5M NaCl. The active fraction was further purified by ammonium sulfate precipitation, followed by dialysis.

The purification was monitored by a peptide degradation assay as follows. All fractions were incubated with iodinated peptide 1 ("$^{125}$I-P1", amino acid sequence HSEVKMDAEF) in 10 mM Tris-HCl (pH 7.6, 1 mM CaCl$_2$) for one hour, and then the cleavage products were separated by TLC on cellulose microcrystalline plates (J. T. Baker), followed by autoradiography (panel C). The TLC solvent was n-butanol:pyridine:acetic acid:water (15:10:3:12 by volume) as described generally in P. Tempst et al. (1983), *Eur. Jour. Biochem.*, Vol. 135, pp. 321–330. Fractions were also reacted with $^{125}$I-P1 for 30 minutes at 4° C., cross-linked with 0.5 mM DSS for 15 minutes at room temperature, and subjected to SDS-PAGE, and the gel was stained with coomassie blue (panel A), dried and exposed to X-ray film (panel B).

Lane identifications in FIG. 1 are as follows: lane 1, Mw standards; lanes 2, 6, 15, DE52 column flow-through fraction; lanes 3, 7, 10, ammonium sulfate ("AS") precipitation, 0–25% saturation; lanes 4, 8, 11, 25–50% AS; lanes 5, 9, 12, 50–75% AS; lane 13, 0.75% AS; lane 14, untreated $^{125}$I-P1. The asterisk (*) indicates the minor 30 Kd band. Further purification, including a 100,000 g spin in PBS followed by solubilization of the pellet in 1% Triton X-100 in PBS and a second spin at 100,000 g, revealed that following these treatments the enzymatic activity is found in both the soluble fraction and the membrane-bound fraction.

Figure 2:
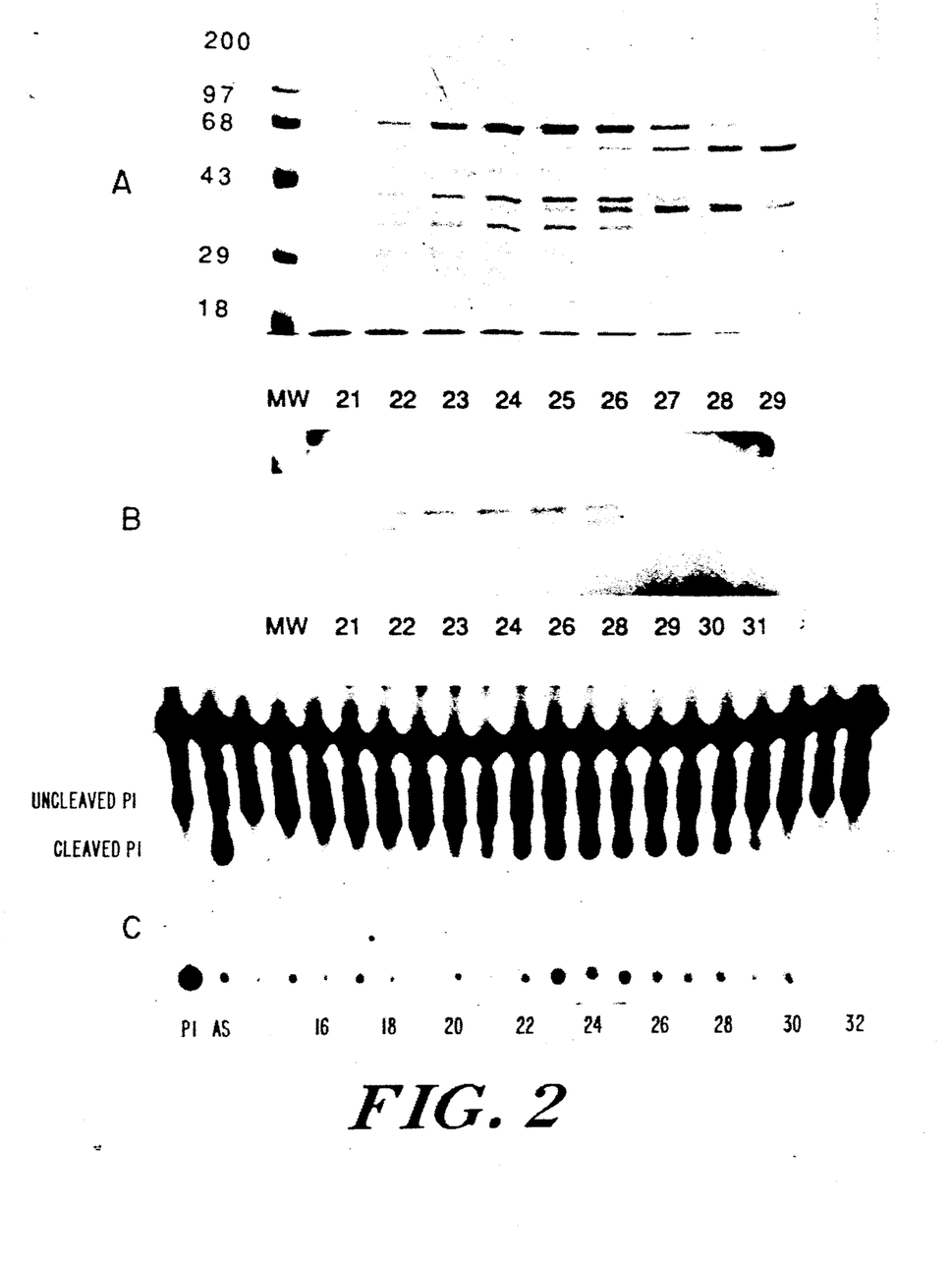
FIG. 2 is a series of prints showing serine protease activity in fractions from brain homogenates from AD patients, further purified by size exclusion chromatography. The respective panels A, B, C are as described in FIG. 1.

Results of purification of a specific serine protease from AD brain by size exclusion chromatography are shown in FIG. 2. An ammonium sulfate fraction 50–75%, obtained as described above, was dialyzed, applied to a mono Q column (Pharmacia) and eluted with a 20–500 mM NaCl gradient in 10 mM Tris HCl, pH 7.0, with 1 mM DDT. Fractions demonstrating activity were concentrated and applied to a Sephadex S-300 column (Pharmacia) and eluted with 10 mM Tris-HCl, pH 7.0, 200 mM NaCl, and 1 mM DDT.

Panels A, B and C in FIG. 2 are as in FIG. 1. Analysis of S-300 column fractions 14 to 32 is shown; fraction numbers are indicated. The first lane in Panel C is untreated $^{125}$I-P1; the second lane is fraction AS 50–75% (before S-300 separation). Fractions 23–28 were reserved for further analysis.

A single protein was radioaffinity labeled (FIG. 1) following initial purification. Subsequent steps of purification resulted in a major protein of approximately 68 Kd (FIGS. 1 and 2) and a minor one at 30 Kd (FIG. 1).

Figure 3:
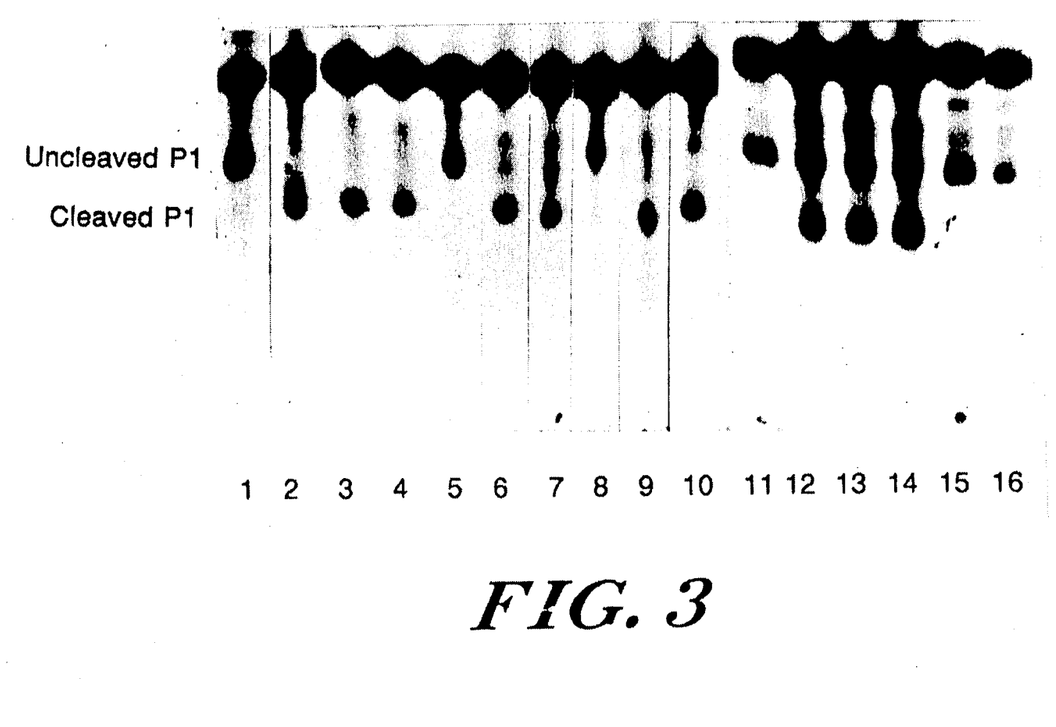
FIG. 3 is a print showing inhibition by various agents of serine protease activity in fractions from brain homogenates from AD patients.

FIG. 3 illustrates effects of inhibitors on the protease activity of the serine AD proteolytic factor isolated as described above. A peptide degradation assay, using 0.1 μg $^{125}$I-P1 for each trial as described above with reference to FIG. 1, was used. Lane identifications in FIG. 3 are as follows: lanes 1 and 11, no protease; lanes 10 and 12, the protease fraction alone ("PF"); lanes 2–9 and 13–16, the protease fraction was treated for 15 minutes at room temperature with various agents, then the P1 was added and the mixture incubated at 37° C. for 1 hour (except lane 9, which was incubated for 20 hours); lane 2, PF with PN1, 1 μM; lane 3, PF with ACT, 0.4 μM; lane 4, PF with ACT, 1 μM; lane 5, PF with ACT, 1.5 μM; lane 6, PF with PN2, 0.2 μM; lane 7, PF with PN2, 0.4 μM; lane 8, PF with PN2, 0.75 μM, for 1 hour;

lane 9, PF with PN2, 0.75 μM, for 20 hours; lane 13, PF with β-mercaptoethanol, 0.5 mM; lane 14, PF with 2 mM $Ca^{2+}$; lane 15, PF with 2 mM EGTA; lane 16, PF with 1 mM DFP.

EGTA, an inhibitor of $Ca^{2+}$ dependent proteases, and DFP, an inhibitor of serine proteases, prevent cleavage of the $^{125}I$-P1 by the AD proteolytic factor (FIG. 3), indicating that the fraction was enriched in a $Ca^{2+}$ activated, serine protease. Additional $Ca^{2+}$ enhances the degradation (FIG. 3, lane 14). In addition, two serine protease inhibitory proteins from human brain that may be involved in regulating the degradation of β-PP, ACT (Calbiochem) and purified PN2 (secreted β-PP), also inhibited cleavage of P1 by the AD proteolytic factor. The complex of the AD proteolytic factor protease with PN2 is reversible; compare lane 8 (1 hr incubation) with lane 9 (20 hrs incubation). In contrast, protease nexin 1 and albumin did not influence the activity of the AD proteolytic factor.

The Kunitz-type protease inhibitors are identical to the inhibitor protease nexin 2 ("PN2", described, for example, in W.E. Van Nostrand et al. (1989), *Nature*, Vol. 341, pp. 546–49; T. Oltersdorf et al. (1989), *Nature*, Vol. 341, pp. 144–47.

Figure 4:
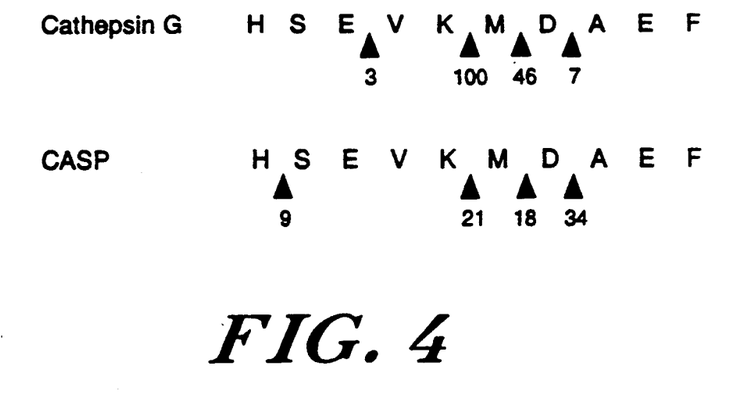
FIG. 4 is a sequence map showing cleavage of P1 by cathepsin G (upper) and by $Ca^{2+}$ activated specific serine protease ("CASP") according to the invention (lower). Abbreviations: H, histidine; S, serine; E, glutamic acid; V, valine; K, lysine; M, methionine; D, aspartic acid; A, alanine; F, phenylalanine. Numerals show percentage cleavage of the peptide bond at each point indicated by an arrow.

Sequences of the peptide 1 cleavage products generated by cathepsin G and some other common proteases were compared to those generated by the serine AD protease fraction; the results of a comparison of P1 cleavage products for $Ca^{2+}$ activated specific serine protease ("CASP") from Alzheimer's disease brain and cathepsin G on peptide 1 are shown in FIG. 4. Five micrograms of unlabeled peptide was incubated with the enzymes in 10 mM Tris-HCl, pH 7.6, 1 mM $CaCl_2$ for 15 hours at 37° C. Resulting mixtures were analyzed by direct peptide sequencing as described generally in P. Tempst et al. (1989), *Anal. Biochem.*, Vol. 183, pp. 290–300; the percentage cleavage of each peptide bond is indicated under the arrows. Unseparated proteolytic fragments were directly sequenced as a mixture. Of the enzymes tested, only cathepsin G and the AD proteolytic fraction cleaved P1 before and after the methionine, and thus only they among these enzymes are capable of generating the cleavage to release the N-terminus of the β-protein from the β-protein precursor. Although cleavage kinetics of the AD proteolytic factor are relatively slow, a presence of active AD proteolytic factor in brain would ensure accumulation of the β-protein over time. The partially purified AD protease cleaves the Asp-Ala bond (FIG. 4) which would result in a β-protein missing the N-terminal Methionine. Cathepsin G is not detectable in human brain tissue using immunohistochemistry or Western or northern blot analysis.

The calcium-activated AD proteolytic factor cleaves metabolically labelled endogenous β-PP substrate as well as the P1 peptide. Labelled $^{35}S$-β-PP, made as described in S. Sisodia et al. (1990), *Science*, Vol. 248, pp. 492–95 and obtained from S. Sisodia, was incubated with the AD proteolytic factor, and the fragments were separated on gel and the gel was autoradiographed. A mixture of proteases appear to be present, and one or more than one of these may play a role in an alternative pathway in the brains of persons having abnormal amyloid deposits.

In addition to being able to degrade the synthetic P1, the serine protease fraction also degraded purified human PN2, and metabolically labeled $^{35}MET$-PN2 secreted into the medium by cells transfected with the human β-PP770. Other labeled secreted proteins were not affected by the protease.

Thus far, two protease inhibitors have been described that may be involved in amyloid deposits of the β-protein type: β-PP (PN2) (the β-protein precursor) and ACT. In the brain, the two forms of the β-PP, one having the protease inhibitory domain (751/770 amino acids) and the other lacking it (695 amino acids), are found in comparable amounts, in contrast to the β-PP in other organs where the inhibitor form prevails. The different ratios of the two forms may explain the almost unique accumulation of the β-protein type amyloid in the brain, although β-protein antibodies can also label skin, intestine and adrenal sections. When the amounts of the β-PP are compared between AD and controls they do not seem significantly different, but high levels of abnormal degradative forms of β-PP are found in AD neurons and neurites and on Western blots using β-PP antibodies.

Use

In AD, and most likely in normal aging, the β-protein is probably formed as a result of an abnormal proteolytic degradation of a normal protein. The finding that the AD cysteine protease cleaves after lysine suggests that it may also be able to cleave at amino acids 15–17 (QKL; Q, glutamine; L, lysine) of the β-protein, the normal physiologic site of β-PP processing. Minor changes in the β-PP, an imbalance in proteases and inhibitors may influence many normal brain processes, for instance neurite extension.

An aberrant proteolytic degradation of the β-PP can contribute to amyloid deposition, which in turn may be trophic or toxic to neurons and astrocytes, causing the neuritic response, neuronal cell death and cognitive deficits. AD may be treated according to the invention by administering to the patient an inhibitor of the AD proteolytic activity according to the invention. Such an inhibitor can be, for example, a competitive inhibitor, such as a fragment of the β-PP molecule corresponding to the binding site of the proteolytic enzyme.

Likely candidates for effective inhibitors of AD proteolytic activity can be screened by incubating an AD protease according to the invention with a known specific substrate (such as a synthetic oligopeptide having an amino acid sequence corresponding to a sequence spanning the β-protein N-terminus) in the presence of a candidate agent under conditions in which the AD protease would be expected, in the absence of an inhibitor, to cleave the synthetic oligopeptide near the N-terminus. Candidate agents that effectively inhibit proteolysis in such a trial can then be tested for inhibitory effect in an in vitro model and/or in an animal model.

A preferred inhibitor is capable of crossing the blood-brain barrier, so that it can be administered parenterally or orally. Also, a preferred inhibitor is a molecule other than a peptide, so that the inhibitor will not be rapidly degraded following administration. Also, the preferred inhibitor specifically inhibits the β-PP cleaving activity of the AD protease, and does not generally inhibit the activity of brain proteases that are essential to normal metabolism.

Proteolytic fragments resulting from the action on β-PP of an AD protease according to the invention can be detected using, e.g., a battery of antibodies directed against the C-terminus and the N-terminus of the β-PP on Western blots. Such analysis can aid in establishing where the β-PP molecule is cleaved and how the β- protein may be generated. Once the production of the β-protein is carried out in vitro, inhibitors (or agents that are candidates for inhibitors) may be screened for capacity to arrest formation of the AD protease in vitro.

Monoclonal antibodies ("mAb") raised against a purified AD protease according to the invention, prepared using standard protocols, can be used to establish (and to quantify) the cellular location of the enzyme in the brain and in other tissues such as skin, kidneys, and liver. Such mAb can also be used in the screening of expression libraries, for locating and identifying AD protease-encoding genes, and for cloning such AD protease genes for use in AD protease-producing expression systems.

The damage to tissues resulting from amyloid deposition in AD appears to be irreversible. The neurological symptoms characteristic of AD appear to result from such tissue damage. For a therapy for AD according to the invention to be effective, it should be employed before amyloid deposition has substantially progressed and before neurological symptoms are manifested.

Determining the presence of, or monitoring the quantity of, AD proteases can provide a tool for early diagnosis of incipient AD. Tissue or body fluid samples such as, for example, samples of blood, CSF, saliva, urine, can be drawn and assayed for the presence of AD proteases, as an indication of a likelihood of abnormal β-PP metabolism, producing β protein and, ultimately, causing amyloid deposition in tissues.

Other embodiments are within the following claims. For example, any crosslinking agent other than DSS can be used in the enzyme purification protocol, provided that the agent is capable of forming crosslinks in an enzyme-substrate complex between portions of the enzyme and the substrate where the enzyme and substrate are in near proximity.

I claim:

1. A brain-derived, calcium activated proteolytic factor comprising a serine protease that cleaves β-protein precursor at a site outside the β-protein domain and near the β-protein N-terminus, said serine protease migrating as a band having a molecular weight of about 30 kDa and a band having a molecular weight of about 68 kDa, as estimated by 12% SDS-PAGE using as molecular weight standards phosphorylase B, bovine serum albumin, ovalbumin and carbonic anhydrase.

2. The proteolytic factor of claim 1; wherein said proteolytic factor cleaves β-PP at a site following a lysine residue or a methionine residue near the β-protein N-terminus.

* * * * *

UNITED STATES PATENT AND TRADEMARK OFFICE
CERTIFICATE OF CORRECTION

PATENT NO. : 5,200,339
DATED : April 6, 1993
INVENTOR(S) : Carmela R. Abraham

It is certified that error appears in the above-indentified patent and that said Letters Patent is hereby corrected as shown below:

Column 1, line 35: please delete "(19897)" and insert therefor -- (1987) --.

Signed and Sealed this

Twelfth Day of April, 1994

Attest:

BRUCE LEHMAN

Attesting Officer

*Commissioner of Patents and Trademarks*

UNITED STATES PATENT AND TRADEMARK OFFICE
CERTIFICATE OF CORRECTION

PATENT NO. : 5,200,339
DATED : April 6, 1993
INVENTOR(S) : Carmela R. Abraham

It is certified that error appears in the above-indentified patent and that said Letters Patent is hereby corrected as shown below:

Column 5, line 14: please delete "10 cm" and insert therefor -- 20 cm --;

Column 5, line 15: please delete "Tris-Cl" and insert therefor -- Tris-Ac --;

Column 5, line 22: please delete "PM" and insert therefor -- YM --;

Column 5, line 25: please delete "66 cm" and insert therefor -- 63 cm --;

Column 5, line 26: please delete "Tris-Cl" and insert therefor -- Tris-Ac --;

Column 5, line 26: please delete "Ph" and insert therefor -- pH --;

Column 5, line 27: please delete "25 ml" and insert therefor -- 10 ml --;

Column 5, line 27: please delete "2.2 ml" and insert therefor -- 2.5 ml --;

Column 7, line 65: please insert -- , -- after "("DDT")";
Column 9, line 55: please delete "labelled" and insert --labeled--.
Column 9, line 56: please delete "Labelled" and insert therefor -- labeled --; and Column 12, line 2: please delete "β protein" and insert therefor -- β-protein --.

Signed and Sealed this

Ninth Day of August, 1994

Attest:

BRUCE LEHMAN

Attesting Officer          Commissioner of Patents and Trademarks